United States Patent [19]
Banik et al.

[11] Patent Number: 5,256,149
[45] Date of Patent: Oct. 26, 1993

[54] TROCAR HAVING TRANSPARENT CANNULA AND METHOD OF USING

[75] Inventors: Michael S. Banik, Cincinnati; Randy R. Stephens, Fairfield, both of Ohio

[73] Assignee: Ethicon, Inc., Somerville, N.J.

[21] Appl. No.: 836,670

[22] Filed: Feb. 14, 1992

[51] Int. Cl.$^5$ ............................................. A61M 5/00
[52] U.S. Cl. ................................. 604/164; 604/158; 604/274
[58] Field of Search .............. 604/165, 158, 164, 272, 604/168, 269, 274

[56] References Cited

U.S. PATENT DOCUMENTS

| | | | |
|---|---|---|---|
| 3,030,953 | 4/1962 | Koehn | 604/168 |
| 4,020,835 | 5/1977 | Nordstrom et al. | 604/168 |
| 4,200,096 | 4/1980 | Charvin | 604/168 |
| 4,601,710 | 7/1986 | Moll | 604/165 |
| 4,645,491 | 2/1987 | Evans | 604/158 |
| 4,654,030 | 3/1987 | Moll et al. | 604/272 |
| 4,772,267 | 9/1988 | Brown | 604/168 |
| 4,902,280 | 2/1990 | Lander | 604/165 |
| 4,976,684 | 12/1990 | Broadnax, Jr. | 604/51 |
| 5,030,206 | 7/1991 | Lander | 604/164 |
| 5,066,288 | 11/1991 | Deniega et al. | 604/51 |
| 5,078,700 | 1/1992 | Lambert et al. | 604/264 |
| 5,127,909 | 7/1992 | Schichman | 604/165 |
| 5,139,485 | 8/1992 | Smith et al. | 604/158 |

OTHER PUBLICATIONS

Brochure OMSLIT1Rev A 022592, ORIGIN Medsystems, Inc.

*Primary Examiner*—Paul J. Hirsch
*Attorney, Agent, or Firm*—Emil Richard Skula

[57] ABSTRACT

A trocar having a trocar obturator and a trocar cannula. The trocar cannula has a cannula tube mounted in a cannula handle, wherein the cannula has an interior passage therethrough. The interior of the trocar cannula is visible through the trocar cannula. The trocar obturator is housed in the trocar cannula for insertion into a body cavity. When used in an endoscopic surgical procedure on a mammal, such that the trocar cannula is inserted into a body cavity and serves as a passageway to and from the body cavity, the interior of the trocar cannula is visible through the cannula so that the passage of instruments, sutures, staples, surgical tissue samples, etc., into and out of the mammalian body cavity through the cannula can be observed by a surgeon during an endoscopic procedure by observing the interior of the cannula at a point exterior to the cannula by looking through the cannula either directly or by using an endoscope.

48 Claims, 8 Drawing Sheets

FIG-1

TROCAR HAVING TRANSPARENT CANNULA AND METHOD OF USING

TECHNICAL FIELD

The field of art to which this invention relates is endoscopic surgery, in particular, trocars having cannulas for use in endoscopic surgical procedures.

BACKGROUND OF THE INVENTION

The use of endoscopic procedures in surgery has become widely accepted. The term endoscopic as used herein is defined to include laparoscopic and arthroscopic. Numerous endoscopic instruments have been developed which allow the surgeon to perform complex surgical procedures with minimal incisions into the skin and tissue surrounding a particular body cavity. In order to introduce the endoscopic instrumentation into the body cavity, it is first necessary to puncture and cannulate the body cavity by using a trocar. Trocars are widely known in the art and typically consist of an obturator and a trocar cannula. Trocars may have a protective housing around the obturator which covers the sharp piercing tip of the obturator prior to and after insertion, and also after removal of the obturator and trocar cannula.

One type of trocar is typically inserted by pressing the distal end of the trocar assembly against the outer skin of the patient with sufficient force to cause the piercing end of the obturator to pierce through the skin, underlying fat, muscle and fascia into the body cavity. Once the surgeon has properly positioned the trocar within the body cavity, the obturator and protective housing are removed, and the trocar cannula is then available as a pathway, e.g., for insertion of endoscopic instrumentation.

Conventionally, trocar cannulas typically consist of a distal cannula tube and a proximal cannula handle. The cannula tube is inserted into a patient along with the obturator, while the proximal handle of the trocar cannula typically remains outside of the patient. Trocar cannula handles typically contain a spring-loaded flapper-type valve which seals the proximal opening of the trocar cannula, thereby allowing the patient's body cavity to remain insufflated with a gas by preventing the gas from escaping through the trocar cannula. The trocar cannula handle typically has an exterior control lever to manually control the position of the flapper valve and to indicate the position of the flapper valve.

As technical know-how is developed, there have been improvements made in the design and construction of trocar cannulas, and surgical techniques involving the use of trocar cannulas in endoscopic procedures have likewise progressed; however, there are deficiencies associated with the use of conventional trocars. In particular, conventional trocar cannulas are made of opaque materials. During an endoscopic surgical procedure, the surgeon has a relatively good view of the targeted surgical site through the use of an endoscope. However, there is one part of an endoscopic surgical procedure which cannot be viewed. Specifically, the insertion of surgical instruments, needles, clips, etc. through the trocar cannula cannot be observed, since as mentioned previously, conventional trocar cannulas are opaque. Similarly, the withdrawal of the instruments, needles, clips, etc., through the trocar cannula cannot be observed.

In addition, it is typical in many endoscopic procedures to remove a tissue specimen from a body cavity through a trocar. Once again, the surgeon loses visual contact with the tissue from the time it enters the distal end of the trocar cannula tube in the body cavity until it exits the proximal end of the trocar cannula handle.

Also, it is not uncommon for a surgeon to lose a needle or a staple within a patient during surgery. This often necessitates a search within the patient for the missing object, prolonging the operative procedure and subjecting the patient to additional risk. During an endoscopic procedure, needles or staples may be accidently lodged in a trocar cannula tube or the trocar cannula handle. Since conventional trocar cannulas are opaque, the surgeon may not realize that the needle or staple has become lodged in the trocar cannula and may search the patient's body cavity in an attempt to retrieve the missing needle or staple. Such a search, although necessary, constitutes a needless risk to the patient.

Additionally, delicate surgical instruments may be damaged during insertion into or removal from a trocar cannula if appropriate care is not taken. It is possible for an instrument to be hung-up and possibly damaged in the trocar cannula handle as the surgeon attempts to maneuver the instrument around the flapper valve and through the trocar handle and into the proximal opening of the trocar cannula tube. Since the handles of conventional trocar cannulas are opaque, this must be done by feel. This deficiency is particularly evident when the surgeon attempts to insert a small diameter instrument through a relatively larger diameter trocar cannula.

Similarly, when attempting to remove tissue specimens through a trocar cannula from a body cavity, it is possible that the surgeon may cause the tissue specimens to be damaged, or the tissue specimens may be disengaged from extraction instruments and released within the trocar cannula, or lodged within the trocar cannula tube or handle, or even fall back into the body cavity. This is further exacerbated by the fact that the surgeon cannot observe the specimen from the time it enters the distal end of the trocar cannula tube until it is withdrawn from the proximal end of the trocar cannula handle.

There are yet additional deficiencies associated with the use of trocar cannulas relating to the flapper valve. Most endoscopic surgical procedures require that the patient's body cavity be insufflated to provide sufficient room to maneuver endoscopic instruments. This is typically done by pressurizing the patient's body cavity with a source of pressurized, sterile gas, e.g., carbon dioxide. This gas is prevented from escaping through trocar cannulas the by the previously mentioned flapper valves and also by gaskets, conventionally contained in trocar cannulas, which engage the outer surfaces of instruments inserted through the trocar cannulas, thereby providing gas-tight seals. However, a slight displacement of a flapper valve in a trocar cannula handle from a fully seated position may be sufficient to cause a gas leak which may result in a rapid volumetric loss of gas from the patient's body cavity. The exact position of the flapper valve in a conventional trocar cannula is not immediately ascertainable by the surgeon, making it more difficult to take immediate action to remedy a gas leak. Flapper valve position indicators are conventionally utilized on trocar cannulas, but the indicators show gross displacement. It is possible to have a slight flapper valve displacement sufficient to allow gas to escape even though the indicator shows that the valve is in a closed position. The displacement may be caused, unknown to the surgeon, by a piece of tissue, or a needle, or a staple being hung-up in the flapper valve assembly. Since the surgeon cannot see the cause of the problem, remediation is difficult and, once again, this introduces an additional, unnecessary risk to the patient. For example, the surgeon, when confronted with a gas leak through the trocar cannula, may be forced to remove the trocar cannula from the body cavity and insert a replacement, again introducing another element of risk to the patient.

Therefore, what is needed in this field are trocar cannulas which overcome the deficiencies associated with conventional trocars. What is also needed is a method of performing an endoscopic surgical procedure which overcomes the deficiencies associated with the use of conventional trocar cannulas.

DISCLOSURE OF THE INVENTION

Accordingly, it is an object of the present invention to provide a trocar cannula for use in endoscopic surgical procedures, and a method of using such a trocar cannula.

Yet another object of the present invention is to provide a trocar, comprising a trocar obturator and trocar cannula assembly, for use in endoscopic surgical procedures and a method of using such a trocar.

It is a further object of the present invention to provide a trocar cannula having a trocar cannula tube and a trocar cannula handle constructed such that the interior of the trocar cannula is visible through the trocar cannula.

It is yet a further object of the present invention to provide methods of performing an endoscopic surgical procedure using a trocar and a trocar cannula of the present invention.

Accordingly, a trocar cannula is provided having an interior visible through the exterior of the trocar cannula. The trocar cannula comprises an elongate cannula tube having a distal end and a proximal end, and a cannula handle. The proximal end of the tube is mounted in the handle. The cannula has a passage therethrough. The cannula may receive an elongate trocar obturator having a tip at its distal end for insertion into a body cavity. After insertion into a body cavity, the trocar cannula provides a pathway allowing access through the trocar cannula to and from the body cavity. The interior of the trocar cannula is visible to an observer when viewed through the exterior of the trocar cannula.

Another aspect of the present invention is a trocar having a trocar cannula wherein the interior of the trocar cannula is visible through the trocar cannula. The trocar comprises an elongate trocar obturator optionally having a piercing tip at its distal end, and an elongate trocar cannula in which the trocar obturator is concentrically housed. An optional protective tube is slideably mounted around the trocar obturator, movable between an extended position and a retracted position, the protective tube being disposed concentrically around the obturator. There is a biasing means acting on the distal end of the protective tube to move the protective tube to the extended position to cover the piercing tip. The trocar cannula comprises an elongate cannula tube and a cannula handle. The tube has a proximal end and a distal end, the proximal end being mounted in the handle. The interior of the trocar cannula tube and cannula handle is visible when viewed through the trocar cannula.

Yet another aspect of the present invention is a method of performing an endoscopic surgical procedure using a trocar cannula of the present invention. The method comprises inserting at least one trocar cannula into a mammalian body cavity. The trocar cannula used in this method has an elongate trocar cannula tube and a trocar cannula handle. The cannula tube has a distal end and a proximal end, the proximal end being mounted in the handle. The interior of the trocar cannula is visible to an observer viewing through the exterior of the trocar cannula. Then, after inserting the trocar cannula, using the trocar cannula as a pathway to the body cavity for performing a surgical procedure, and observing the interior of the trocar cannula during at least part of the procedure.

Yet another aspect of the present invention is a method of performing an endoscopic surgical procedure using a trocar and trocar cannula of the present invention. The method comprises inserting at least one trocar into a body cavity of a mammal wherein the trocar comprises an elongate trocar obturator housed in a trocar cannula. The trocar cannula used in this method has an elongate trocar cannula tube and a trocar cannula handle. The trocar cannula comprises a tube having a proximal and a distal end, and a handle. The proximal end is mounted int the handle. The interior of the trocar cannula is visible to an observer viewing through the exterior of the trocar cannula. Then, after inserting the trocar, removing the obturator from the trocar cannula and using the trocar cannula as a pathway to and from the body cavity for performing a surgical procedure, and observing the interior of the trocar cannula during at least part of the procedure.

Yet another aspect of the present invention is a method of using the above-described trocar and a method of using the above-described trocar cannula.

Other features and advantages of the invention will become more apparent from the following description and accompanying drawings.

BEST MODE FOR CARRYING OUT THE INVENTION

The disclosure of U.S. Pat. No. 5,066,288 is incorporated by reference.

Figure 1:
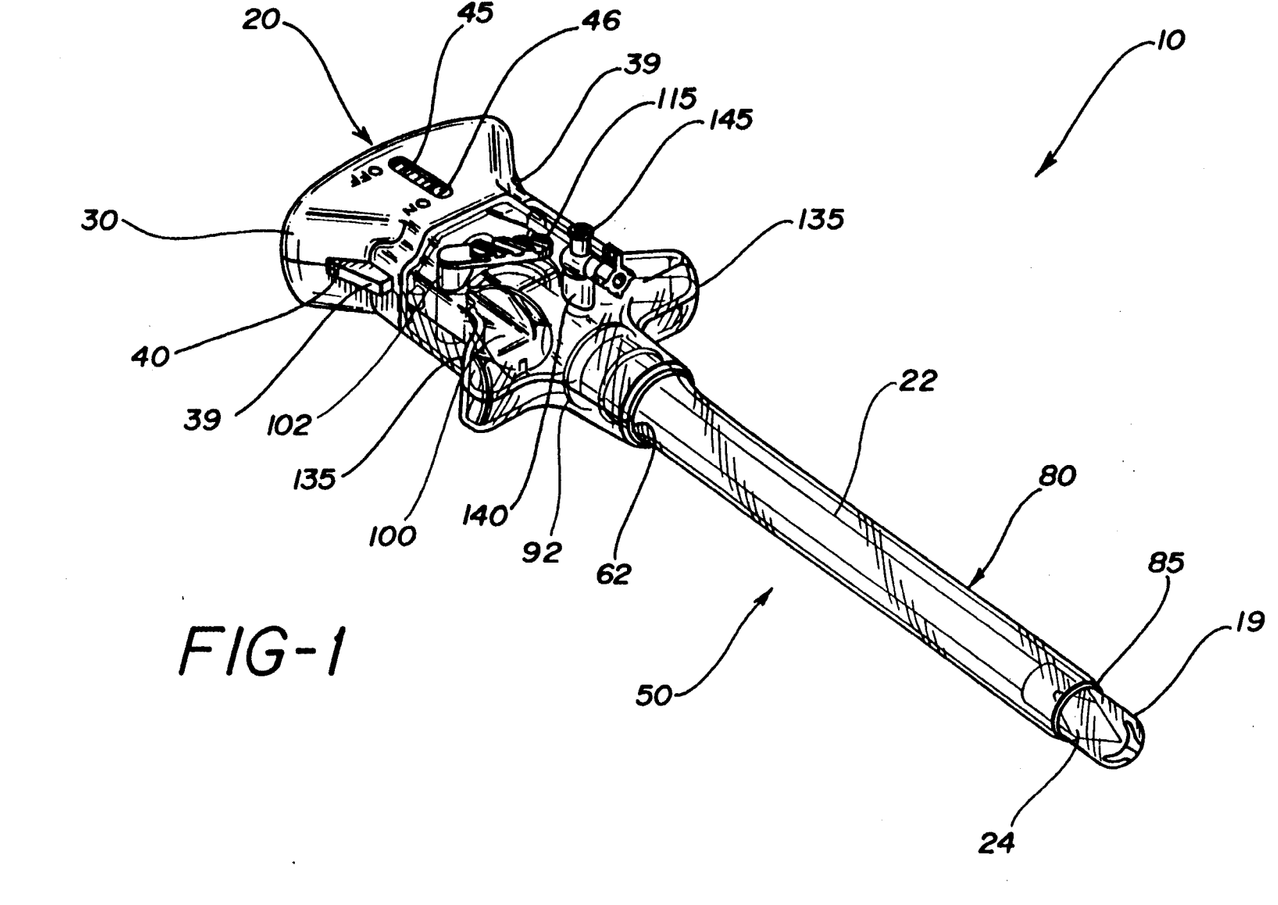
FIG. 1 is a perspective view of an embodiment of a trocar of the present invention.
Figure 2:
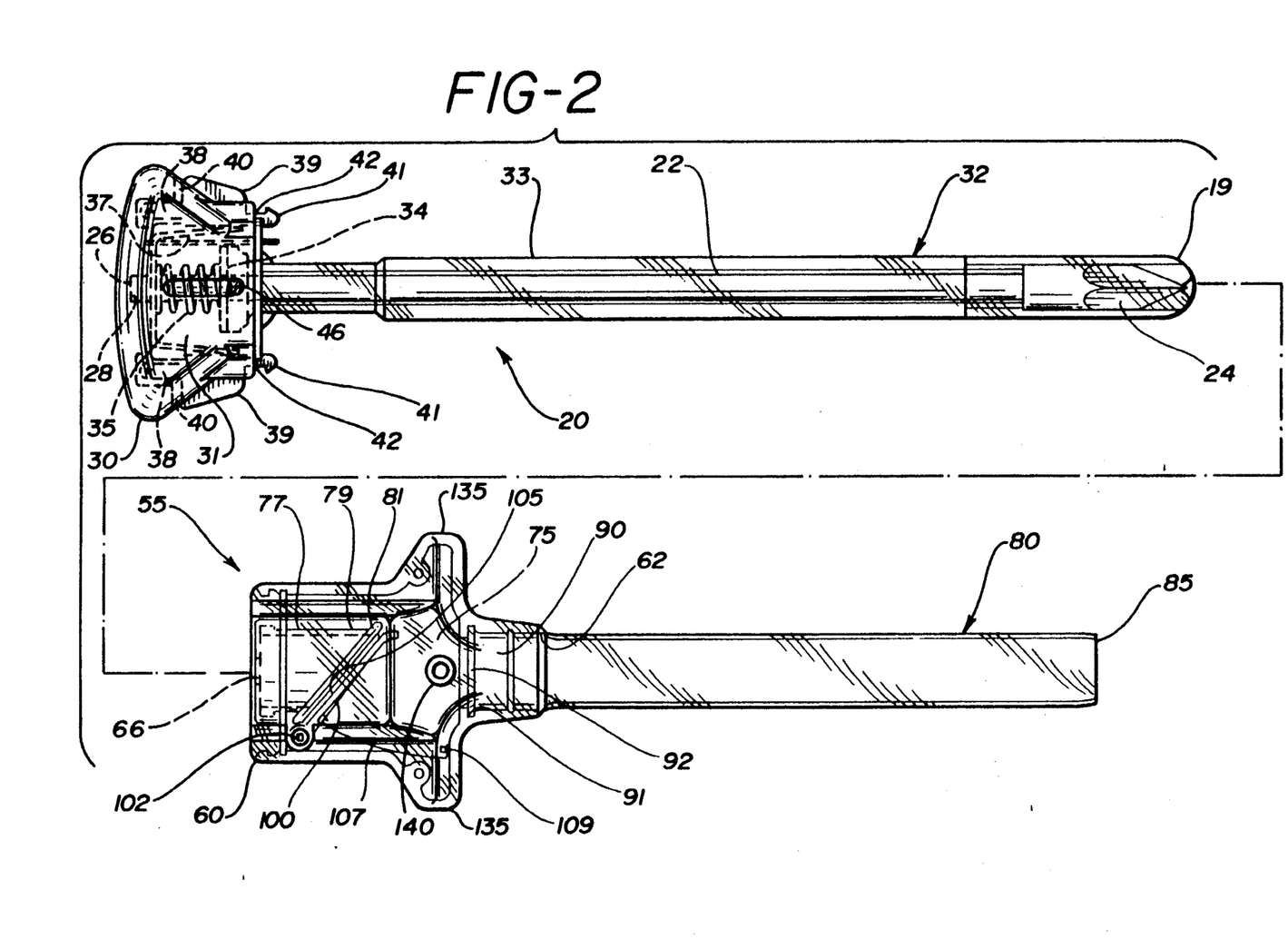
FIG. 2 is a plan view of a trocar obturator and trocar cannula of the present invention.

A trocar 10 of the present invention is shown in FIG. 1 and FIG. 2. Trocar 10 is seen to have trocar cannula 50 and trocar obturator 20. The trocar obturator 20 can be seen through the trocar cannula 50.

Figures 3, 4:
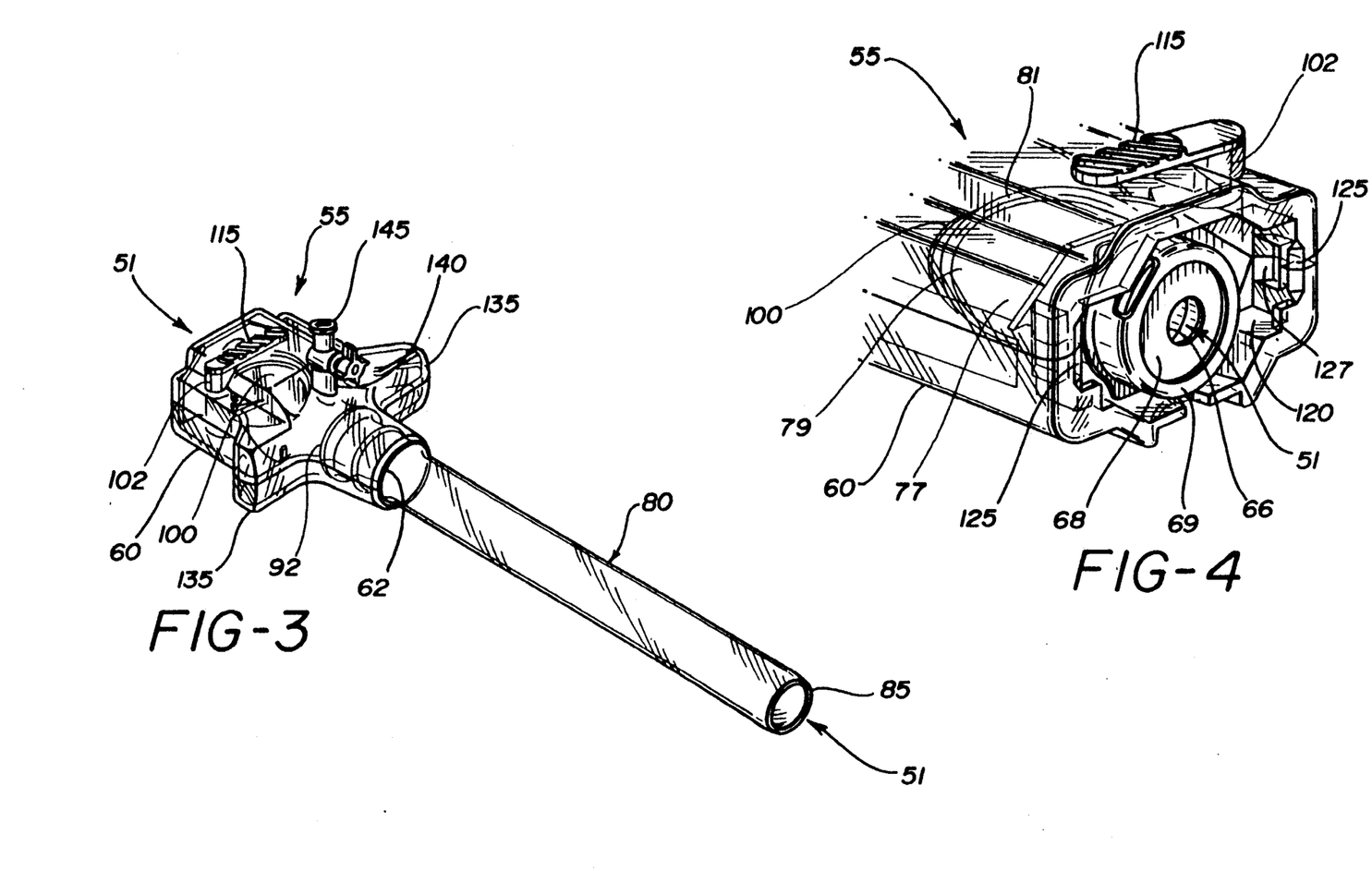
FIG. 3 is a perspective view of a trocar cannula of the present invention.
FIG. 4 is an enlarged, partial perspective of the distal end of the trocar cannula handle.

Referring to FIGS. 1, 2 and 3, trocar cannula 50 is seen to have trocar cannula tube 80 and trocar cannula handle 55. Trocar cannula 50 has passageway 51 therethrough for receiving various members such as trocar obturators, conventional surgical instruments and the like. Trocar cannula tube 80 is an elongate tube having open distal end 85 and open proximal end 90. Proximal end 90 has flange 92 for mounting in trocar cannula handle 55. Trocar cannula handle 55 has hollow housing 60. In the distal end of housing 60, there is annular groove 91 for receiving flange 92 of trocar cannula tube 80. Housing 60 has distal aperture 62 for receiving proximal end 90 of trocar cannula tube 80. As seen in FIG. 4, proximal aperture 66 is located in the proximal end of housing 60 for receiving a gasket ring 68. Gasket ring 68 is mounted about the aperture 66 and is retained by the retaining member 69.

Cavity 75 within housing 60 contains tubular passageway 77 which extends from proximal aperture 66 into the cavity 75 in a distal direction along the longitudinal axis of the trocar cannula 50. Cavity 75 is in communication with tube 80. The distal end 79 of tubular passageway 77 is angulated. A sealing ring 81 mounted to distal end 79 of tubular passageway 77 forms a valve seat which contacts the face 105 of flapper valve 100. Flapper valve 100 is pivotally mounted on pin 102 and biased rearward against sealing ring 81 by spring member 107 in order to provide a gas-tight seat. One end of spring member 107 is mounted in the interior distal wall of housing 60 at 109. Pin 102 extends through the top of housing 60. Pivotally mounted lever 115, which is mounted to the top of pin 102, indicates the position of flapper valve 100 between a closed position and a fully open position. The proximal end of housing 60 has external proximal cavity 120 in which gasket ring 68 and retaining member 69 are mounted. Proximal aperture 66 is surrounded by cavity 120. Tabs 125 project inwardly from opposite side walls of the housing 60 surrounding cavity 120. Cavities 127 are disposed distal to the tabs 125 in the walls of housing 60. Tabs 125 and cavities 127 form part of a locking mechanism for locking together the trocar obturator 20 and the trocar cannula 50 to form the trocar 10.

As can be seen in FIG. 1, FIG. 2, and FIG. 3, frame 60 of trocar cannula handle 55 projects outwardly on both sides toward the distal end of frame 60 to form finger grips 135 Between finger grips 135, tubular section 140 extends upwardly from the top of frame 60 to form a channel in communication with cavity 75. Valve 145 is mounted to tubular section 140. Valve 145 may be any type of conventional valve, although it is preferred to use a plug valve. Valve 145 may be used, for example, as a means to insufflate and desufflate.

Referring to FIG. 1 and FIG. 2, trocar obturator 20 is seen to have an elongate shaft 22 having a sharpened distal piercing point 24. The proximal end 26 of shaft 22 is mounted in cavity 28 contained in the interior, proximal wall of trocar obturator handle 30. Trocar obturator handle 30 is hollow, containing interior cavity 31.

Optional safety shield 32 is slideably mounted on shaft 22 and has tube member 33 concentrically disposed about shaft 22. Safety shield 32 also has end flange 34 mounted to the proximal end of tube member 33. The proximal end of safety shield 32 is slideably mounted and contained within cavity 31 of handle 30.

A coil spring 35 is concentrically mounted to the proximal end of shaft 22 and abuts on one end against the interior proximal wall of handle 30 and on the other end against flange 34. Coil spring 35 provides a distal biasing force against flange 34 of slideably mounted safety shield 32 so that safety shield 32 is moveable between a fully extended position, wherein the piercing point 24 of obturator 20 is covered, and a fully retracted position, wherein piercing point 24 is exposed. In the fully extended position, end flange 34 abuts the interior, distal wall of handle 30. Levers 38 are pivotally mounted in handle 30. The levers 38 have grips 39 extending outwardly through slots 40 in the side walls of handle 30 and tab members 41 extending distally through slots 42 in the distal wall of handle 30. Levers 38 are biased outwardly by leaf spring 37. Slot 45 extending though the top of the handle 30 exposes position indicator member 46 extending upwardly into slot 45 from the top of flange 34 to which the bottom end of member 46 is mounted.

In a particularly preferred embodiment, safety shield 32 will have a bullet shaped nose 19 at the distal end. Although not shown in the drawings, the trocar handle 30 may contain an optional conventional locking mechanism or equivalent thereof which causes the optional safety shield 32 to lock in the extended position (covering the piercing point 24) after the trocar 10 has been inserted into a body cavity or removed therefrom.

Figure 7:
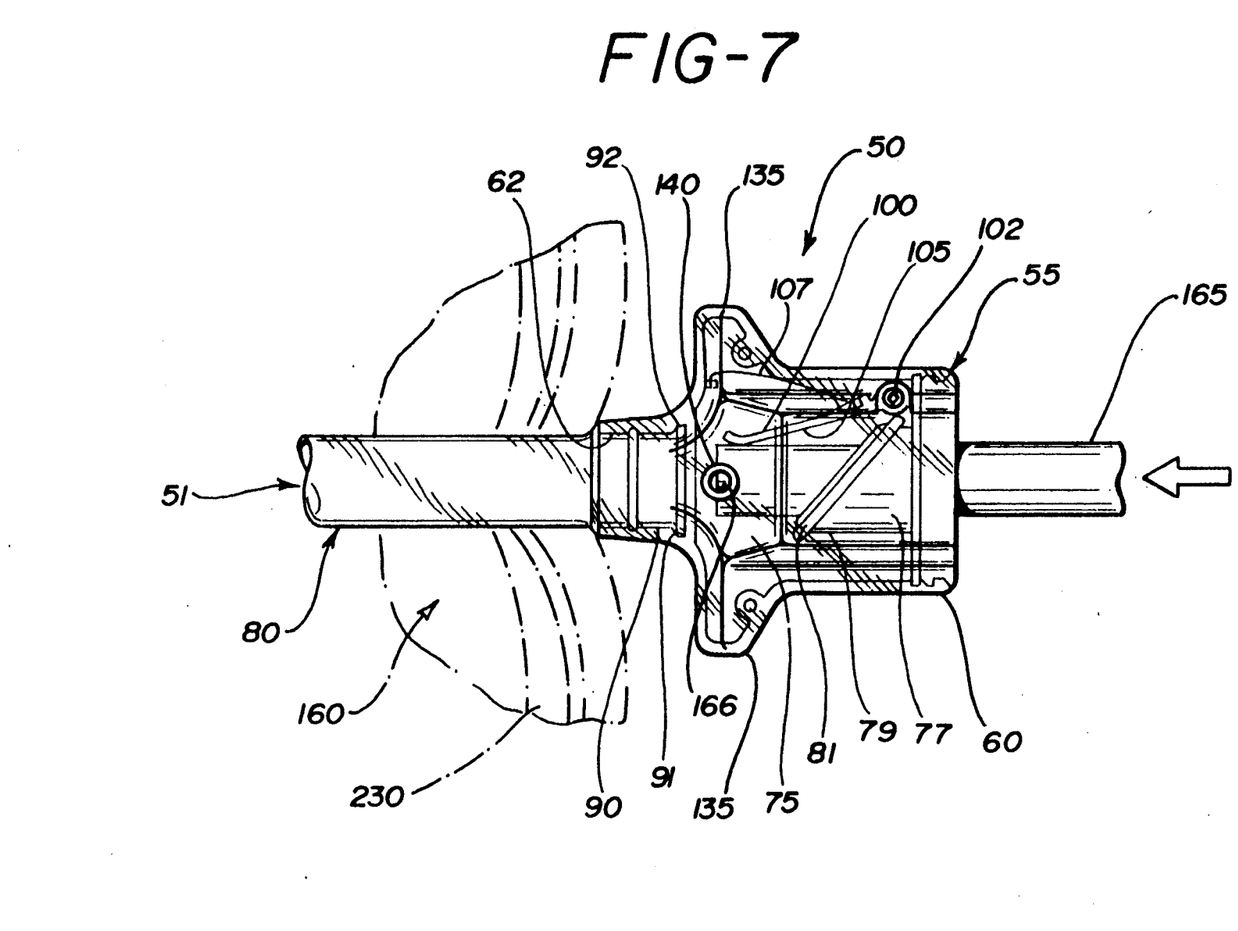
FIG. 7 illustrates a trocar cannula of the present invention inserted through the abdominal wall of a mammal, and further illustrates the interior of the trocar cannula handle as a surgical instrument is maneuvered therethrough.

The trocar 10 is assembled for use by inserting the distal end of obturator 20(e.g., the bullet nose 19) into aperture 66 of housing 60 through gasket ring 68. Gasket ring 68 is sized to sealingly engage safety shield 32 (and various endoscopic instruments) by displacing radially outwardly and axially. As the bullet shaped nose 19 of the safety shield 32 contacts the proximal face 105 of flapper valve 100, it causes flapper valve 100 to pivot distally about pin 102 to an open position, as seen in FIG 7. The shaft 22 and the safety shield 32 are then slid through the cavity 75, into and through the aperture 62 and into trocar cannula tube 80. A sufficient axial force applied in a distal manner against the handle 30 of trocar obturator 20 causes the tab members 41 to be displaced inwardly by tabs 125. As the trocar obturator is moved further axially within the trocar cannula 50, tab members 41 are displaced by the outward bias of spring 37 into cavities 127 contained in the side walls of housing 60 in cavity 120, thereby locking the trocar obturator 20 within the trocar cannula 50.

The trocar 10 operates in the following manner. Bullet nose 19 of safety shield 32 is placed into contact with the exterior skin of a mammal such that the longitudinal axis of trocar 10 is substantially perpendicular to the surface of the skin, although the axis can be angulated at acute or obtuse angles with respect to the skin surface. A forward or distal force is applied against the trocar handle 30 causing the safety shield 32 to displace proximally against coil spring 35 thereby exposing piercing point 24.

Piercing point 24, along with safety shield 32 and cannula tube 80 are pushed through the exterior skin and underlying fat, muscle and fascia into the underlying body cavity. Once the piercing tip 24 and bullet nose 33 enter the body cavity, the biasing force applied by compressed spring 35 causes the safety shield 32 to slide distally to an extended position, thereby covering piercing point 24.

Trocar obturator 20 is removed from trocar cannula 50 by pivotally displacing the tab grips 39 in obturator handle 30 inwardly, thereby releasing tab members 41 from cavities 127. Simultaneously, a proximal or pulling force is applied to the handle 30 of trocar obturator causing the obturator to slide out of the trocar cannula 50. As the bullet nose 19 enters tubular passageway 77, the face 105 of flapper valve 100 is displaced against sealing ring 81 by spring 107 and seated, thereby sealing off the tubular passage 77 and producing a gas-tight seal.

Figure 8:
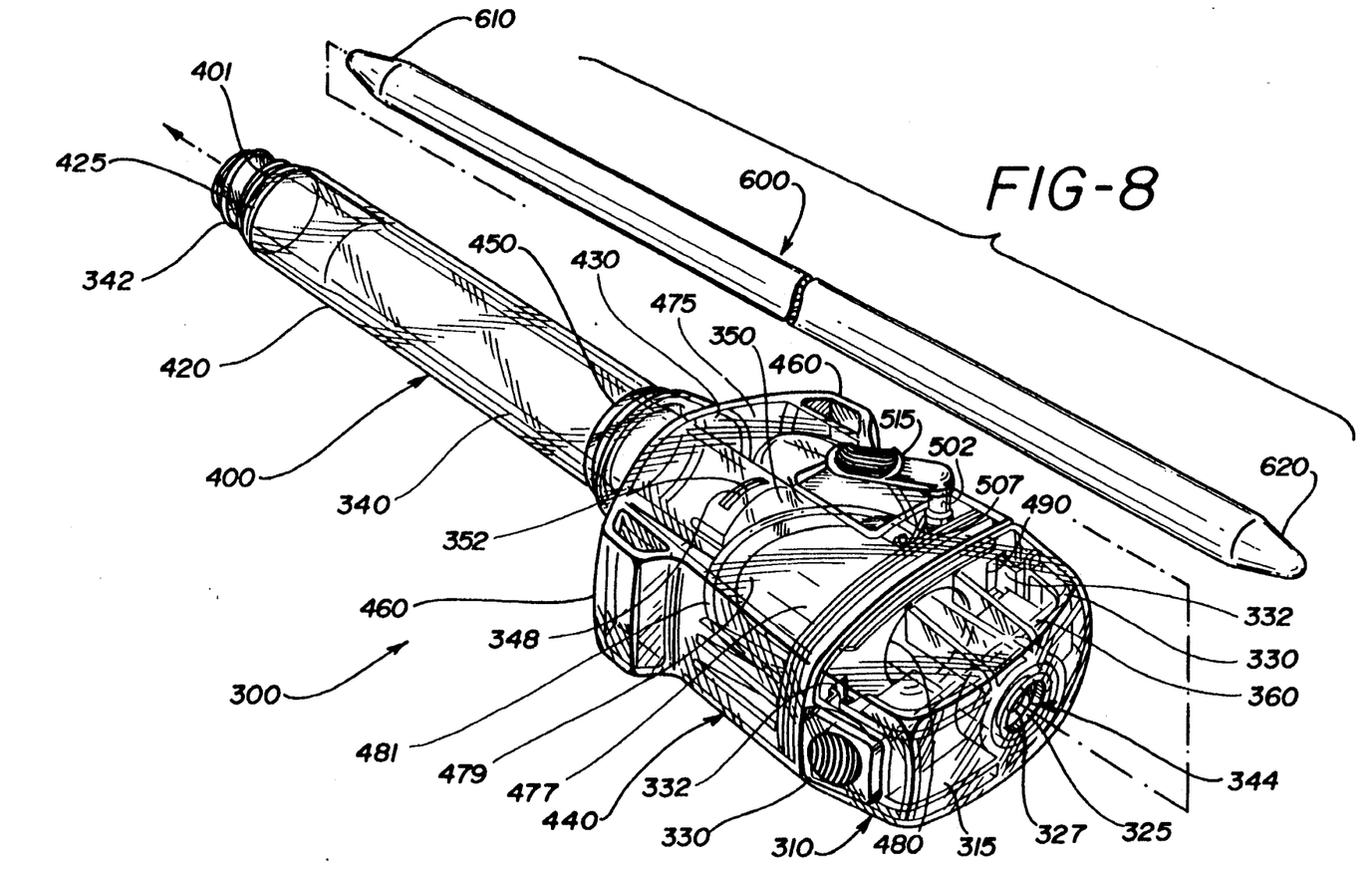
FIG. 8 is a perspective view of an alternate embodiment of a trocar obturator and trocar cannula assembly of the present invention.
Figure 9:
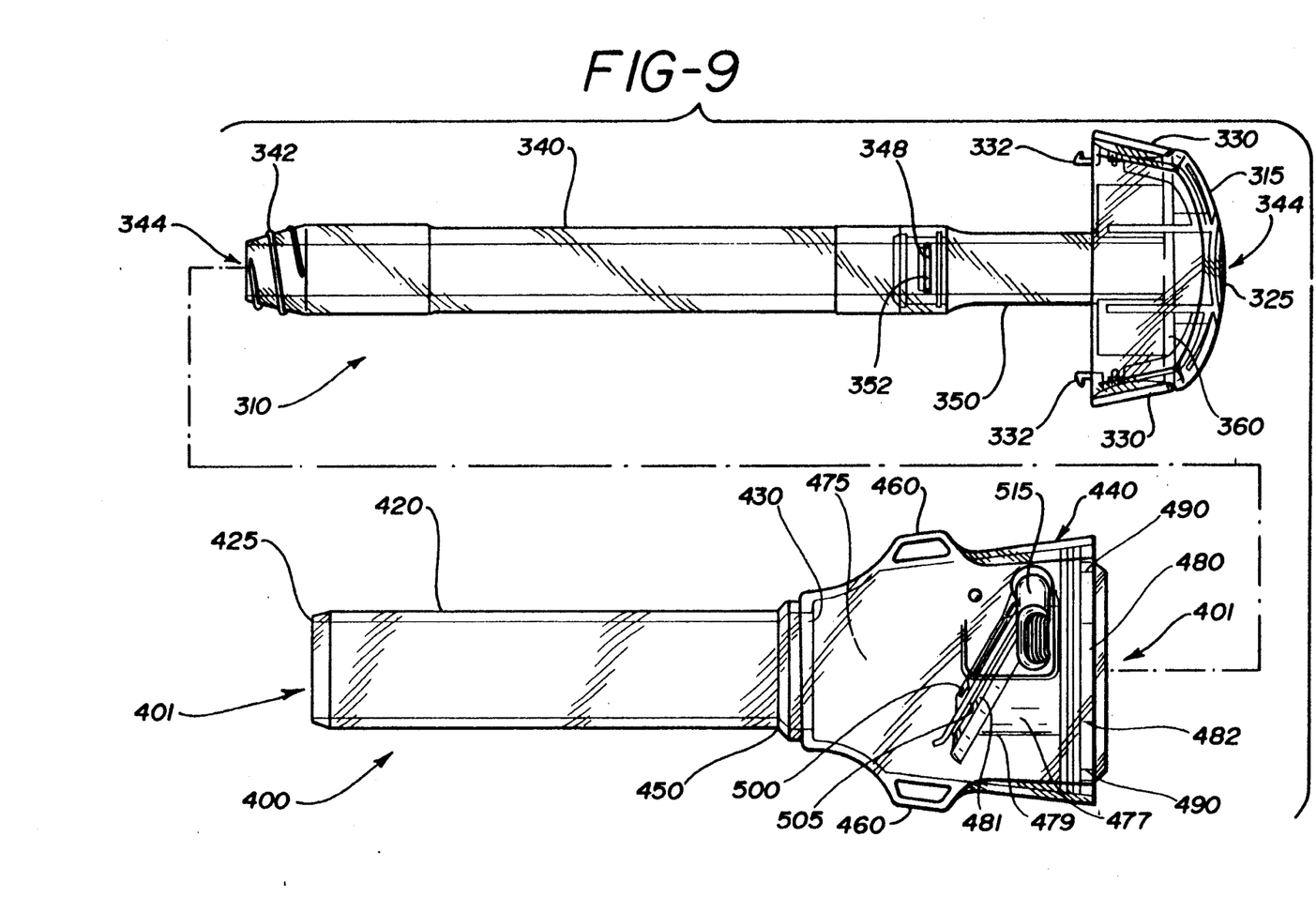
FIG. 9 is a plan view of the trocar obturator and trocar cannula of FIG. 8.

Another embodiment of a trocar of the present invention is seen in FIG. 8 and FIG. 9. The trocar 300 of the present invention as seen in FIG. 8 and FIG. 9 is typically a trocar having a larger inner diameter trocar cannula (about 18 mm to about 33 mm or larger) than the trocar cannula of a trocar having a cutting piercing tip (about 11 mm–12 mm). As can be seen in FIG. 8 and FIG. 9, the trocar 300 has a trocar obturator 310 and a trocar cannula 400.

The trocar obturator 310 has a handle 315 and an obturator 340 which is mounted to the handle 315 by obturator mounting head 350. The trocar obturator handle 315 has rear aperture 325 in which seal 327 is mounted. Aperture 325 is in communication with the passage 344 running through trocar obturator 310. The obturator 340 is an elongated tube having a screw-threaded distal end 342. Obturator 340 is mounted at its proximal end to tubular obturator mounting head 350. Obturator 340 is mounted and engaged by the tubular mounting head 350 through the slots 348 contained in the proximal end of obturator 340 and through tabs 352 contained on the distal end of mounting head 350. Tabs 352 are lockingly engaged by slots 348. The proximal end of mounting head 350 is affixed to the proximal wall of handle 315 and is in communication with aperture 325. The mounting head 350 is seen to have beam member 360 which protrudes through either side of the handle 315. Tab actuating buttons 330 are connected to either end of the beam 360 in a living hinge-type arrangement. Tab members 332 are seen to extend distally from each tab button 330. Actuation of the tab buttons 330 will allow the obturator 310 to be removed from the trocar cannula 400 by causing the tab members 332 to be rotated inwardly.

Once again, referring to FIG. 8 and FIG. 9, it can been seen that the trocar cannula 400 has elongate trocar cannula tube 420 which is mounted in trocar handle 440. Cannula 400 has a passage 401 therethrough. Trocar cannula tube 420 has distal opening 425 and proximal opening 430. The handle 440 has distal aperture 450 for receiving the proximal end of cannula tube 420. The distal end of trocar cannula tube 420 is mounted in the distal end of handle 440 through aperture 450. The trocar cannula handle 440 has proximal aperture 480 in which sealing ring 482 is mounted. Cavity 475 within handle 440 contains tubular passageway 477 which extends from the proximal aperture 480 into the cavity 475 in a distal direction along the longitudinal axis of the trocar cannula 400. Distal end 479 of tubular passageway 477 is angulated. A sealing ring 481 mounted to the distal end 479 forms a valve seat which contacts the face 505 of flapper valve 500. Flapper valve 500 is pivotally mounted on pin 502 and biased rearward by spring member 507. Lever 515, mounted to the top of pin 502, indicates the position of the flapper valve 500, and is primarily used to manipulate the flapper valve. It can be seen in FIG. 8 that the flapper valve 500 is in the open position by looking through the trocar cannula handle 440. The proximal end of the trocar cannula handle 440 contains cavities 490 for receiving the tabs 332 on the trocar obturator 310. Finger grips 460 extend from either side of the cannula handle 440. The interior of the trocar handle 400 is visible through the trocar cannula.

The trocar obturator 310 and trocar cannula 400 are assembled to form trocar 300, and disassembled, in a manner similar to that previously described for trocar 10.

As can been seen in FIG. 8, the trocar 300 contains a passage therethrough for receiving exchange rod 600. Exchange rod 600 is an elongate rod having blunted distal end 610 and proximal end 620.

In order to use the trocar 300 of the present invention, the following procedure is typically followed. Initially, a trocar having a piercing tip, such as the trocar 10 of the present invention is inserted into a body cavity. Then, the trocar obturator 20 is removed leaving the trocar cannula 50 positioned in the body cavity. Next, the distal end 610 of exchange rod 600 is inserted into and through the trocar cannula 50. Next, the trocar cannula 50 is removed from the body cavity, and slid off of the exchange rod 600 while the exchange rod 600 remains inserted into the body cavity. At this point, the distal end 610 of exchange rod 600 is protruding through the trocar incision into the body cavity, while the proximal end 620 is exterior to the body cavity. Next, the distal end of the trocar 300 is placed over the proximal end 620 of the exchange rod 600 and is slid down along the exchange rod until the distal tip 342 of the obturator 310 makes contact with the skin surrounding the body cavity. Next, the trocar 300 is screwed into and through the musculature, fascia and underlying tissue surrounding the body cavity until the trocar cannula tube 420 is disposed in a position proximal to the target surgical site. Then, the tabs 330 on the trocar obturator handle 315 are displaced inwardly and a proximal backward force is placed upon the trocar handle 315 while grasping the exchange rod 600 such that the tabs 332 are disengaged from the cavities 490, and the trocar 310 and the exchange rod 600 are removed, simultaneously, from the body cavity and from the trocar cannula 400. As the obturator tube 340 and the exchange rod 600 exit cannula handle 440, flapper valve 500 is seated against seal ring 489. This provides a trocar cannula 400 having a larger pathway to and from the body cavity than the initial trocar cannula 50.

Referring to FIG. 7, a trocar cannula 50 of the present invention is seen inserted through a body wall 230 adjacent to a body cavity 160 of a mammal. The handle 55 of trocar cannula 50 is positioned exterior to the body wall 230. The interior of the handle 55 is visible though the handle 55. The distal end 166 of an endoscopic surgical instrument 165 (such as an endoscope) is visible through the trocar handle 55 and is observed as it is maneuvered through flapper valve 100, through the cavity 75 and toward the proximal end 90 of trocar cannula tube 80 through aperture 62. The position of flapper valve 100 is visible through the handle 55. It will be noted that for the purpose of illustration, valve 145 is not shown but tubular section 140 is seen. Typically valve 145 is required.

Figure 5:
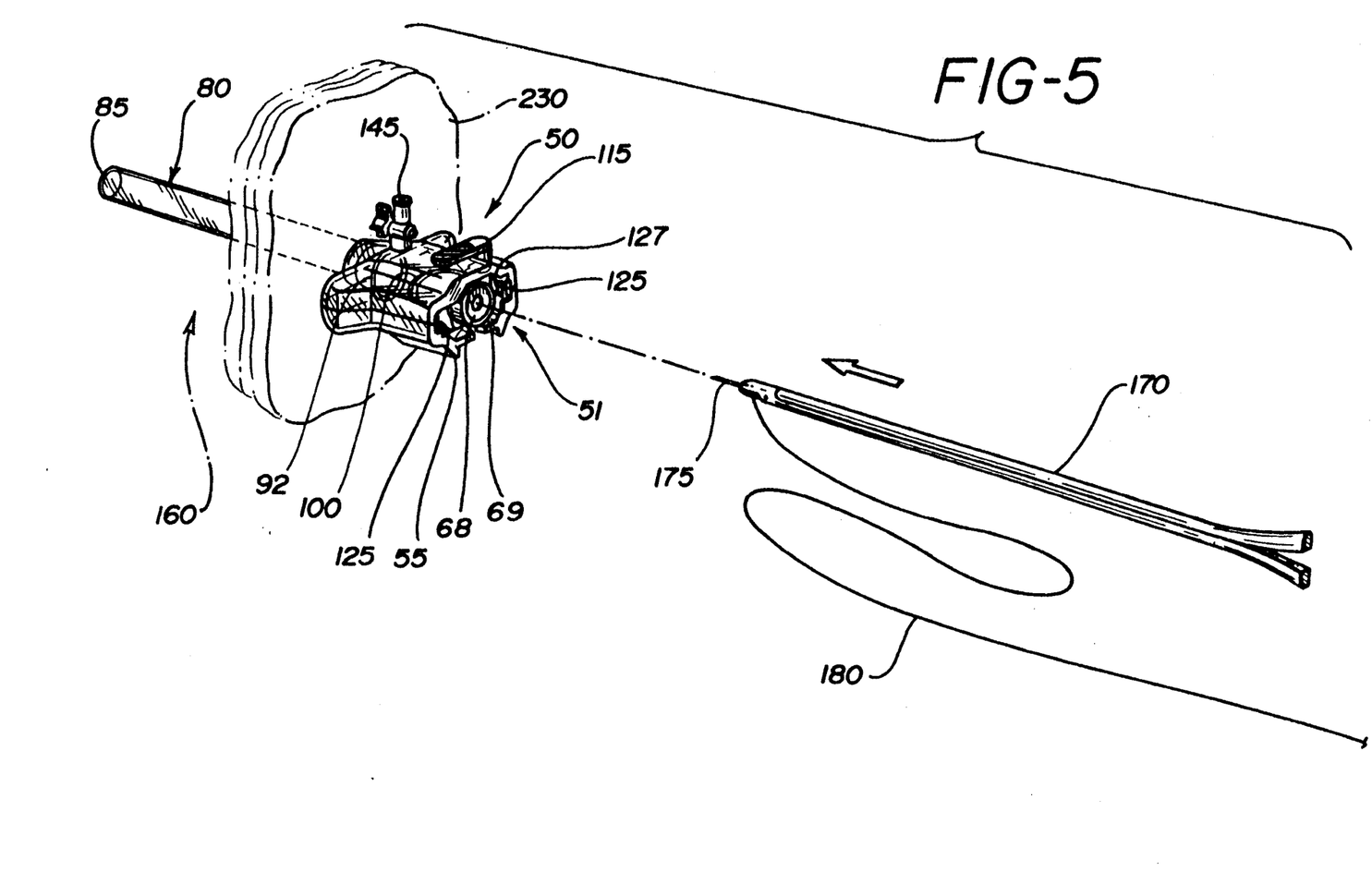
FIG. 5 illustrates a trocar cannula of the present invention inserted into a body cavity of a mammal after removal of the trocar obturator, and prior to insertion of an endoscopic suture and needle held by a needle grasper.

A trocar cannula 50 of the present invention, as seen in FIG. 5, is shown inserted through a mammalian body wall 230 into a body cavity 160. An endoscopic needle grasper 170, an endoscopic needle 175 and a suture 180 are seen prior to insertion into trocar cannula 50. The interior of the trocar cannula 50 is visible through the cannula walls. The position of flapper valve 100 is also visible through the cannula.

Figure 6:
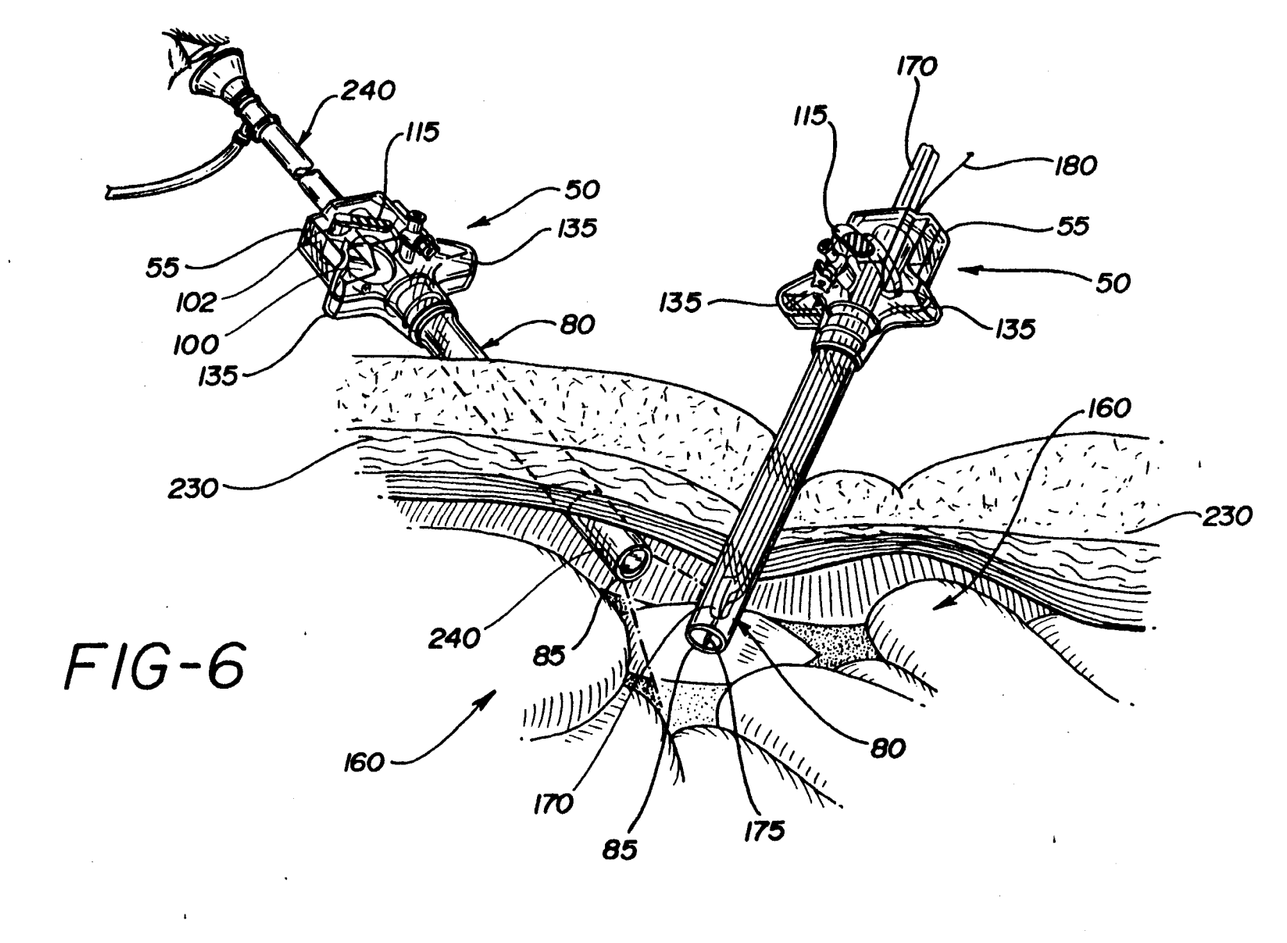
FIG. 6 illustrates a surgical instrument placed through the trocar cannula into a body cavity and visible through the trocar cannula tube and trocar cannula handle.

Referring to FIG. 6, two trocar cannulas 50 of the present invention are seen positioned though a body wall 230 and into a mammalian body cavity 160. The first trocar cannula 50 is seen inserted into the body cavity 230 through which an endoscope 240 has been inserted. The position of flapper valve 100 is visible through the handle 55, and, the endoscope 240 is visible through handle 55 and through tube 80. The endoscope may be configured to output to a video monitor. An endoscopic needle grasper 170, an endoscopic needle 175 and a suture 180 are seen inserted in the second trocar cannula 50. The grasper 170 and suture 190 are visible directly through the handle 55. The end of the grasper 170, the needle 180 and suture 190 are seen through the trocar cannula tube 80 via the endoscope 240.

Trocars are conventionally used to provide access to a surgical site in a patient's body cavity. The trocar is typically inserted by pressing the distal end of the trocar against the outer skin of the patient. The insertion site is selected by the surgeon to provide optimal access to the target surgical site within the body cavity. Sufficient force is applied to the trocar handle in a direction along the longitudinal axis of the trocar so that the piercing tip of the trocar obturator effectively penetrates the patient's skin, underlying fat tissue, muscle and fascia. Although, larger diameter trocars such as trocar 300 are inserted as previously described. The distal end of the trocar is then located by the surgeon to a position effective for access to the target surgical site. Then the trocar obturator is removed through the proximal end of the trocar cannula by applying a rearward force to the trocar handle. The trocar cannula is then used as a passageway to and from the patient's body cavity.

Referring to FIG. 5., FIG. 6, FIG. 7, and FIG. 8, it can be seen that when using the trocar cannulas of the present invention having an interior visible through the cannula, the surgeon may observe the passage of surgical instruments, staples, needles, sutures, electrodes, tissue and tissue samples, pharmaceuticals, and any and all other medical devices or drug delivery systems into, through and out of the trocar cannula. As seen in FIGS. 5-8, for example, the surgeon may observe the interior of the trocar cannula 50 directly through the portion of the trocar cannula 50 located exterior to the patient, typically the trocar cannula handle 55, or indirectly, using an endoscope 240, through the trocar cannula tube 80 located within the body cavity 160. The surgeon may also observe the trocar obturator 20 of the trocar 10 of the present invention during insertion. The trocars 10 of the present invention are easier to see with an endoscope 240 compared to conventional trocars, thereby facilitating insertion and positioning within the body cavity 160. This improved visibility assists in preventing damage to, or displacement of, internal organs which may be caused by the insertion of the trocar. The trocar cannulas 50 of the present invention may be used for insufflation and desufflation by manipulating the flapper valve 100 or the insufflation valve 145. The position of the flapper valve 100 and its condition, as well as the seal ring 81, are visible through the trocar cannula handle 55. The position of flapper valve 500 is similarly visible through the handle 440.

The endoscopic surgical method of the present invention uses the trocars of the present invention, such as trocar 10 and trocar 300, having trocar cannulas with an interior visible through the trocar cannula, such as trocar cannulas 50 and 400 of the present invention. The surgical method initially involves the preparation of the patient and insertion of a trocar of the present invention, e.g., trocar 10, into a body cavity of the patient, using conventional endoscopic surgical techniques. Endoscopic surgical techniques are disclosed in the *Textbook Of Laparoscopy*, Jaroslav F. Hulka, M.D., Grune and Stratton, Inc., New York (1985), and in—*Laparoscopy For Surgeons*, Barry A. Salky, M.D., IGAKUSHOIN Medical Publishers, New York (1990), which are incorporated by reference. The trocar obturator 20 is then removed and the trocar cannula 50 is available as a passageway to and from the body cavity 160, as seen in FIG. 5, FIG. 6 and FIG. 7. When using a trocar cannula of the present invention such as trocar cannula 50, it can be seen that the trocar cannula handle 55 is typically disposed exterior to the body wall 230 while the distal end 85 of the cannula tube 80 is within the body cavity 160. Various conventional endoscopic surgical instruments, surgical staplers, sutures, needles, pharmaceuticals, tissue, tissue samples, drug delivery devices, electrosurgical devices, electrodes, etc., are inserted through the trocar cannula 50 and maneuvered to the target surgical site where conventional endoscopic surgical techniques are utilized.

In the endoscopic surgical methods of the present invention, the surgeon visually observes the passing and maneuvering of the previously mentioned devices, tissue and the like into, through and out of the trocar cannulas of the present invention, for example trocar cannula 50, having a visible interior during at least part of the procedure. This is done by direct observation through the portion of the trocar cannula 50 which is exterior to the patient, typically the trocar cannula handle 55, and through indirect observation via an endoscope through the trocar cannula tube 80 which is inside of the patient's body cavity 160.

The visual input available to the surgeon when using the surgical method of the present invention allows the surgeon to maneuver more readily through the trocar cannula 50. The surgeon is also able to visually monitor the position of the flapper valve 100 to determine whether the flapper valve 100 is properly seated. In addition, the trocar cannula 50 and the flapper valve 100 may be monitored for objects which may become lodged within the trocar cannula handle 55, the cannula tube 80, or about the flapper valve 100 such as staples, needles, tissue, etc. The surgeon can also take immediate action to clear such objects by inserting a suitable grasping instrument into the trocar cannula 50, maneuvering the instrument to the site of the object, then grasping the object and removing it from the trocar cannula 50 passage. When the surgical procedure is completed at the target surgical site, all instruments, needles, excess staples, excess suture, free tissue and the like are removed through the trocar cannula while the surgeon observes the interior of the trocar cannula 50 during at least part of the procedure. Then the trocar cannula 50 is removed and the insertion site is closed using conventional techniques such as suturing, surgical stapling, dressing the incision with tape or combinations thereof. Although this discussion of surgical procedures referred to trocar 10 and trocar cannula 50, it is equally applicable to all trocars of the present invention including trocar cannula 400 and trocar 300.

Various types of endoscopic surgical techniques can be performed using the trocars of the present invention in the thoracic and abdominal cavities. The surgical techniques include conventional endoscopic procedures such as cholesystectomy, appendectomy, vagatomy, hysterectomy, wedge resection of the lung, anastomosis, and herniagraphy and the like. The surgical method of the present invention is, however, applicable to all endoscopic surgical procedures.

The trocar cannulas of the present invention may be constructed using conventional manufacturing techniques from any conventional, medical grade material which allows the interior of trocar cannula to be visible through the trocar cannula. Transparent, plastic materials such as polycarbonate, acrylates, urethanes, polyvinylchlorides, and copolymers thereof as well as clear composite resins or co-extruded resin systems systems and the like are typically used. Transparent is defined to mean the ability to pass light through a material so that it is possible to see through the material.

It is particularly preferred to use transparent polycarbonate material. Other transparent materials such as glass may be used if one were willing to accept any attendant disadvantages. The transparent materials may, if so desired, be colored with sufficient amounts of conventional dyes and pigments, including radioopaque, effective to color the the transparent material, while retaining its transparency. It is contemplated that the trocar cannulas of the present invention are preferably constructed entirely of transparent material. However, the cannulas may also be constructed using conventional manufacturing techniques partly of conventional opaque materials and partly with a sufficient amount of transparent materials effective to allow the interior of the trocar cannula to be visible when viewed from certain perspectives from the exterior of the cannula. For example, along the longitudinal axis of the trocar cannula 50, half of the cannula could be transparent, and the other half opaque. Additionally, transparent windows having various shapes can be located in the trocar cannula tube 80 and trocar cannula handle 55.

If one skilled in the art were willing to accept whatever disadvantages might be present, the trocar cannulas of the present invention ,e.g., trocar cannula 50, can be constructed with either the trocar cannula handle 55 or trocar cannula tube 80 having a visible interior, while the other piece is constructed from an opaque material.

The thickness of the walls of the trocar cannulas of the present invention will be sufficiently thick to effectively provide the required mechanical strength, yet allow the interior of the trocar to be visible through the trocar cannula. The wall thicknesses will depend upon the diameter of the trocar cannula tube and its length as well as the size of the cannula handle. Mechanical strength is defined to mean those mechanical characteristics conventionally required for effective functioning of a trocar including bending strength, resistance to buckling, shear strength, maximum allowable deflection under maximum load, thermal expansion and contraction, shell strength, pressure rating, safety factors and the like.

The following examples are illustrative of the principles and practice of the present invention.

EXAMPLE 1

A pig of conventional size and weight was prepared for surgery using conventional techniques including depilation of the epidermis in the region of expected incision, scrubbing and rinsing with conventional fluids, and application of a conventional iodine solution. The animal was placed in a recombant position on a conventional operating table and covered with a sterile drape. The animal was anesthetized with a sufficient dose of a conventional anesthetic effective to induce an anesthetized state.

The animal was cannulated with an endotracheal tube and connected to a conventional anesthesia machine and ventilated as required. The abdominal cavity of the animal was insufflated in a conventional manner with carbon dioxide and several conventional trocars were inserted into the abdominal cavity; and, the obturators were removed so that the trocar cannulas remained in the abdominal cavity. An endoscope was inserted through one of the trocar cannulas. The endoscope was connected to a video monitor. Then an exchange rod 600 was inserted into one of the conventional trocar cannulas and the trocar cannula was removed leaving the distal end 610 of the exchange rod 600 in the body cavity. An 18 mm trocar 300 of the present invention was placed over the exchange rod 600 and positioned within the body cavity by screwing the trocar obturator end 342 through the body wall and into the body cavity where the cannula tube 420 was positioned proximal to the target surgical site. The exchange rod 600 and trocar obturator 310 were then simultaneously removed and the 18 mm trocar cannula 400 was used as a pathway to the body cavity.

A colectomy was performed. Various instruments were inserted through the 18 mm trocar cannula 400 including an 18 mm staple/cutter apparatus, and 5 mm and 10 mm graspers. The interior of the 18 mm trocar cannula 400 was observed during the procedure as instruments were inserted through and removed from the trocar cannula 400. The interior of the trocar cannula tube 420 was observed using the endoscope while the interior of the trocar cannula handle 440 was observed directly by the surgeon.

The 18 mm trocar cannula 400 used was the trocar cannula of the present invention. The trocar cannula tube 420 and trocar cannula handle 440 were constructed of clear, transparent polycarbonate so that the interior of the trocar cannula tube 480 and the interior of the trocar handle 440 were visible through the trocar cannula. The trocar cannula 400 had sufficient wall thicknesses to effectively provide required mechanical strength while retaining transparency. The flap valve 500 was visible when instruments were inserted into and removed from the trocar cannula 400. Similarly, the interior of the trocar cannula tube 420 and part of the interior of the patient with surgical instruments inserted into the trocar cannula were visible through the trocar cannula tube by endoscope during the surgical procedure.

EXAMPLE 2

A human patient is prepared for surgery using conventional preparatory techniques and is effectively anesthetized using a sufficient dose of a conventional anesthetic. The patient is connected to conventional anesthesiology equipment, and as needed, ventilation equipment. After using conventional endoscopic preparatory procedures, including insufflation and insertion of an endoscope, a trocar 10 of the present invention is inserted into the abdominal cavity of the patient by pressing the distal end of the trocar 10 onto the exterior skin of the patient in the proximity of the target surgical site. Sufficient force is exerted by the surgeon on the trocar handle 30 effective to cause the piercing tip 24 of the trocar obturator 20 to pierce through the patient's skin and underlying fat, muscle tissue, and fascia thereby bringing the end of the trocar into a position in the body cavity 160 which is in the proximity of the target surgical site. The surgeon is able to easily observe the distal end of the trocar 10 as it enters the body cavity 160 via an endoscope 240, allowing the surgeon to more precisely position the trocar 10 and avoid damage to internal organs. The trocar obturator 20 is then removed from the trocar cannula 50. An incision is made in the target site using a conventional endoscopic instrument and a piece of tissue is removed by grasping the tissue with a grasper and extracting the tissue through the trocar cannula 50. The surgeon observes on the endoscope video monitor the tissue as it enters into and is maneuvered through the trocar cannula tube 80. The surgeon visually observes, directly, the tissue as it is guided through the trocar cannula handle 55, through the flapper valve 100, and out of the distal end 66 of the trocar cannula handle 55. During the surgical procedure, the surgeon observes the flapper valve 100 in the trocar handle to check that the valve 100 is properly seated.

The surgeon then inserts an endoscopic surgical needle and suture, using an endoscopic suture grasper, through the trocar cannula 50. The surgeon is able to guide the suture grasper, needle and suture through and around the cannula handle 55 and flapper valve 100 and into cannula tube 80 by direct observation of the interior of cannula 50. The surgeon sutures the incision at the target surgical site, using conventional endoscopic surgical techniques, and removes the surgical needle and excess suture through the trocar cannula. The surgeon visually observes the needle and suture as it passes through the trocar cannula handle 55 during insertion and removal, and visually guides the needle and suture around the flapper valve 100 and into and out of the trocar cannula tube 80.

Using the endoscope, the surgeon observes the needle and suture passing through the trocar cannula tube 80 during insertion and removal.

Next the trocar cannula 50 is removed and the trocar insertion site is closed by conventional taping, suturing, and/or stapling techniques. During the operation the surgeon is able to observe visually, either directly or via the endoscope, the interior of the trocar cannula tube 80 and the interior trocar cannula handle 55. Additionally, the surgeon is able to visually observe the flapper valve 100 during the operation to assure that it is properly seated.

There are many advantages associated with the trocars of the present invention having a trocar cannula which allows the interior of the trocar cannula to be seen from an external observation point through the walls of the trocar cannula. For the first time, the insertion of endoscopic instruments, sutures, staples, drug delivery devices, pharmaceuticals, etc. through a trocar cannula and the extraction of the endoscopic instruments, sutures, staples, tissue specimens, etc., out through a trocar cannula can now be seen by the surgeon by observing the interior of the trocar cannula through the trocar cannula. In contrast, conventional trocar cannulas are constructed from opaque materials and therefore do not allow the interior of the trocar cannula to be observed through the trocar cannula.

Frequently, during the course of an endoscopic procedure, it is necessary for the surgeon to remove staples, needles, etc., from the patient's body cavity. It is not unusual for staples, needles, etc., to become accidently lodged by the surgeon in the trocar cannula. In the conventional trocar cannula, the surgeon has no way of seeing that the needle or staple is lodged in the trocar cannula. The surgeon must then look for the missing needle or staple, assuming it was lost inside the patient, thereby perhaps needlessly prolonging the operation and exposing the patient to needless risk. The trocar cannulas of the present invention allow the surgeon to have a virtually unrestricted view of the interior of the trocar cannula through the trocar cannula. A staple or needle which is lodged in the trocar cannula tube of the present invention would be immediately observed by the surgeon on the endoscope monitor. Similarly, a needle or staple which is lodged in the handle of the trocar cannula could be seen directly by the surgeon. In either case, the surgeon can, based upon this additional visual input, take immediate action to remove the lodged object, thereby eliminating both an unnecessary search for the object and the associated risk to the patient.

Another advantage of the trocar cannulas of the present invention, e.g., the trocar cannula 50, is the visibility of the flapper valve 100 in the trocar cannula handle 55. The flapper valve 100 functions such that it displaces (by pivoting) in order to allow the insertion of endoscopic instruments. When an instrument is withdrawn, the flapper valve 100 closes and provides a gas tight seal. A slight displacement of the flapper valve 100 from a fully seated position will result in a gas leak. This displacement may be caused by a needle, a staple or tissue, etc., becoming lodged between the flapper valve 100 and the flapper valve seat formed by seal ring 81. Although conventional trocar cannulas have flapper valve position indicators, the indicators are typically not sensitive enough to alert the surgeon to a slight displacement. The problem can be remediated if the surgeon is able to detect it. Conventional trocars which experience leakage must be removed and replaced if the leak cannot be stopped. This prolongs the operation and exposes the patient to additional risk. The trocars, trocar cannulas and methods of the present invention eliminate this problem by allowing the surgeon to observe and inspect the flapper valve while the cannula remains inserted in the body cavity. This visual input, regarding the condition of the interior of the trocar cannula, allows the surgeon to perform immediate action to dislodge an object from the flapper valve or trocar handle and to re-seat the valve to a gas tight condition. The length of the operative procedure is reduced since a new cannula does not have to be introduced into the patient and the associated risk to the patient is eliminated.

Yet another advantage of the trocars, trocar cannulas and methods of the present invention is that tissue specimens may be easily maneuvered through the trocar cannulas. As mentioned previously, when using conventional opaque trocars, the surgeon has no visual input from the time the tissue enters the distal end of the trocar cannula tube until the tissue specimen is maneuvered past the flapper valve and through and out of the distal end of the trocar cannula handle. Tissue samples may become damaged or lost in a conventional trocar cannula. In addition, lost tissue may fall back through the trocar into the body cavity. For example, the samples may become lodged in the flapper valve. The trocar cannulas and methods of the present invention help to overcome these problems by allowing the surgeon to easily maneuver tissue samples through the trocar cannulas. The surgeon, when using, for example, the methods, trocar 10 and trocar cannula 50 of the present invention, can observe a tissue sample from the moment that the tissue sample enters the distal end 85 of the cannula 50 up to the moment that the tissue sample is maneuvered out of the proximal end of the cannula handle 55. This enhanced maneuverability eliminates or minimizes the possibility of damage to tissue as it is extracted through a trocar cannula. Tissue which is damaged may be unusable, requiring the surgeon to again perform a tissue extraction, once again needlessly prolonging the operative procedure and exposing the patient to additional risk. The use of the trocar cannulas and methods of the present invention reduces or eliminates damage to, or the loss of, extracted tissue. Often, the loss or damage of a tissue specimen can be critical and even life threatening, for example, in the extraction of a potentially cancerous tissue specimen.

There are yet additional advantages associated with the trocar cannulas and methods of the present invention. It is common to use electrosurgical devices to perform endoscopic surgical techniques such as electrocutting and coagulating tools. If these tools have faulty insulation, grounding, resulting in a visible electrical arc or discharge, occurs upon insertion of the electrosurgical device into the patient. Arcing of electrosurgical tools resulting from improper insulation is potentially life threatening. In a conventional trocar cannula, the arc would not be visible until after the electrosurgical tool exits the distal end of the trocar cannula tube, and, the opaque cannula tube may screen the surgeon's view of any arcing exterior to the cannula tube. When utilizing the trocar cannula and method of the present invention, an electrical arc can be observed immediately upon insertion into the trocar cannula. In addition, after insertion arcing can be seen through the trocar cannula. The surgeon can then withdraw the faulty device prior to the commencement of any electrosurgical procedures. This minimizes the patient's exposure to any faulty, electrosurgical equipment, thereby further reducing an extremely dangerous risk to the patient.

Frequently, delicate, fragile laparoscopic instruments must be inserted through and removed from a trocar cannula. Examples of such instruments include graspers, dissectors, needle holders, suture loop appliers, clip appliers, cautery devices, laser wires or guides, stapling instruments, endoscopic cameras and other such instruments. It is possible for such instruments to be damaged during insertion into, and removal from, a conventional trocar cannula. As mentioned previously, the insertion and removal of instruments through and from the conventional trocar cannula is the single phase of an endoscopic procedure during which the surgeon has no visual input, yet this phase can be quite critical. The instruments must be guided through the conventional trocar cannula by feel. Referring to FIG. 7, one skilled in the art will appreciate that an instrument must be carefully maneuvered through and/or about the flapper valve 100, the insufflation valve channel 140, in the handle housing 60 and the proximal aperture 90 of cannula tube 80. As the instrument 165 is maneuvered though the flapper valve 100, it is possible, for example, for the distal end 166 of the instrument to strike the distal end of the interior of the cannula handle housing 60 on either side of the proximal opening 90 of the cannula tube 80, which may result in damage to the instrument if the surgeon attempts to force the instrument through to the cannula tube 80. The trocars, trocar cannulas, and methods of the present invention allow the surgeon to maintain visual contact, either directly or via endoscope, with an instrument throughout its entire passage through a trocar cannula. Such continuous visual contact substantially reduces the risk of damaging instruments, thereby improving the ability of the surgeon to perform the endoscopic surgical procedure. In addition, there is a reduced possibility of the instrumentation damaging the trocar cannula, for example the flapper valve, since the surgeon can visually observe passage through the trocar.

Yet another advantage of the trocar cannulas and methods of the present invention is that the trocar insertion and removal is, surprisingly and unexpectedly, facilitated. Light from an endoscope within the body cavity readily illuminates the trocar cannula tube of the present invention, i.e., the trocar cannula may have light conducting properties. This allows easier insertion and replacement in comparison to conventional trocars having opaque cannula tubes. This improved visibility decreases the risk associated with inserting and removing trocar cannulas. That risk may include the surgeon inadvertently piercing internal organs and blood vessels.

It can be seen that the trocars, trocar cannulas and methods of the present invention have numerous advantages over conventional trocars and trocar cannulas as well as methods using such conventional trocars and trocar cannulas. A very significant result of these advantages is that many deficiencies associated with conventional cannulas and methods are eliminated or greatly reduced.

Although this invention has been shown and described with respect to detailed embodiments thereof, it will be understood by those skilled in the art that various changes in form and detail thereof may be made without departing from the spirit and scope of the claimed inventions.

What is claimed is:

1. A trocar cannula having an interior passage therethrough, comprising
   an elongate trocar cannula tube; and,
   a trocar cannula handle for mounting said cannula tube,
   wherein the interior passages of said trocar cannula tube and trocar cannula handle are visible through the tube and handle.

2. The trocar cannula of claim 1 wherein the handle additionally comprises valve means for sealing off the passage.

3. The trocar cannula of claim 2 further comprising sealing means mounted about the entrance to the cannula handle for sealingly engaging a member inserted therethrough.

4. The trocar cannula of claim 1, wherein the cannula comprises a transparent material selected from the group consisting of polycarbonates, acrylates, urethanes, polyvinylchlorides, copolymers thereof, clear composite resins, and co-extruded resins.

5. The trocar of claim 4 wherein the material comprises polycarbonate.

6. The cannula of claim 1 wherein the cannula walls comprise sufficient thickness to effectively provide mechanical strength while remaining transparent.

7. The cannula of claim 1 additionally comprising a sufficient amount of a pigment or dye effective to tint the cannula while allowing the interior of the cannula to remain visible through the cannula.

8. A trocar, comprising
an elongate trocar obturator having a proximal end and a distal end, said distal end having a tip;
an elongate trocar cannula having an interior passage therethrough for receiving the trocar obturator, said cannula comprising an elongate trocar cannula tube and a trocar cannula handle for mounting said cannula tube,
wherein the interior of the trocar cannula is visible through the trocar cannula.

9. The trocar of claim 8 wherein the obturator comprises a sharp piercing tip at its distal end.

10. The trocar of claim 9 further comprising
a protective tube having a distal end and a proximal end slideably mounted around the trocar obturator, moveable between an extended position and a retracted position, said protective tube being disposed concentrically around said obturator; and
biasing means acting on the proximal end of the protective tube to move the tube to the extended position to cover the piercing tip.

11. The trocar of claim 8 wherein the trocar cannula further comprises valve means for sealing off the passage.

12. The trocar of claim 11 wherein the trocar cannula further comprises sealing means mounted about the entrance to the cannula handle for sealingly engaging a member inserted therethrough.

13. A method of performing an endoscopic surgical procedure on a mammal using a trocar, comprising
inserting a trocar into a body cavity, said trocar comprising a trocar cannula having a passage therethrough, and, an elongate trocar obturator, wherein said trocar cannula comprises an elongate trocar cannula tube, having a distal end and a proximal end, and a trocar cannula handle for mounting the proximal end of the trocar cannula tube, wherein the interior of the trocar cannula is visible through the cannula;
removing the trocar obturator from the trocar cannula;
using the trocar cannula as a pathway to and from the body cavity in order to perform an endoscopic surgical procedure within the body cavity; and
observing the interior of the cannula through the cannula during at least part of the procedure.

14. The method of claim 13 wherein the trocar comprises a sharp, distal piercing tip.

15. The method of claim 13 wherein the trocar obturation further comprises
a protective tube, having a distal end and a proximal end slideably mounted around the obturator, moveable between an extended position and a retracted position, said protective tube being disposed concentrically around the obturator; and,
biasing means acting as the proximal end of the protective tube to move the tube to the extended position to cover the piercing tip.

16. The method of claim 13 wherein the trocar cannula further comprises valve means for sealing off the passage.

17. The trocar of claim 13 wherein the trocar cannula further comprises sealing means mounted about the entrance to the cannula handle for sealingly engaging a member inserted therethrough.

18. The trocar cannula of claim 13, wherein the cannula comprises a transparent material selected from the group consisting of polycarbonates, acrylates, urethanes, polyvinylchlorides, copolymers thereof, clear composite resins, and co-extruded resins.

19. The trocar of claim 18 wherein the material comprises polycarbonate.

20. The trocar cannula of claim 13 wherein the cannula tube comprises an interior visible through the tube and the handle is opaque.

21. The trocar cannula of claim 13 wherein the handle comprises an interior visible through the handle and the tube is opaque.

22. The cannula of claim 13 wherein the cannula walls comprise sufficient thickness to effectively provide mechanical strength while remaining transparent.

23. The cannula of claim 13 additionally comprising a sufficient amount of a pigment or dye effective to tint the cannula while allowing the interior of the cannula to remain visible through the cannula.

24. A method of performing an endoscopic surgical procedure on a mammal using a trocar cannula having a passage therethrough, comprising
inserting a trocar cannula into a body cavity, wherein said trocar cannula comprises an elongate trocar cannula tube, having a distal end and a proximal end, and a trocar cannula handle for mounting the proximal end of the trocar cannula tube, the interior of the cannula being visible through the cannula;
using the trocar cannula as a pathway to and from the body cavity in order to perform an endoscopic surgical procedure within the body cavity; and
observing the interior of the cannula through the cannula during at least part of the procedure.

25. The method of claim 24 wherein the trocar cannula further comprises valve means for sealing off the passage.

26. The trocar of claim 24 wherein the trocar cannula further comprises sealing means mounted about the entrance to the cannula handle for sealingly engaging a member inserted therethrough.

27. The trocar cannula of claim 24, wherein the cannula comprises a transparent material selected from the group consisting of polycarbonates, acrylates, urethanes, polyvinylchlorides, copolymers thereof, clear composite resins, and co-extruded resins.

28. The trocar of claim 27 wherein the material comprises polycarbonate.

29. The trocar cannula of claim 24 wherein the cannula tube comprises an interior visible through the tube and the handle is opaque.

30. The trocar cannula of claim 24 wherein the handle comprises an interior visible through the handle and the tube is opaque.

31. The cannula of claim 24 wherein the cannula walls comprise sufficient thickness to effectively provide mechanical strength while remaing transparent.

32. The cannula of claim 24 additionally comprising a sufficient amount of a pigment or dye effective to tint the cannula while allowing the interior of the cannula to remain visible through the cannula.

33. In a method of using a trocar in an endoscopic surgical procedure, the trocar comprising an elongate trocar obturator and an elongate trocar cannula having a passage therethrough, the method comprising inserting the trocar into a mammalian body cavity, and removing the obturator from the cannula, and using the cannula as a passageway to the body cavity for insertion of an endoscopic surgical instrument within the cannula, the improvement comprising using a transparent trocar cannula wherein the interior of the trocar cannula is visible through the trocar cannula and observing the instrument within the interior of the cannula during at least part of the procedure.

34. The method of claim 33 wherein the trocar obturator comprises a sharp, distal piercing point.

35. The method of claim 33 wherein the trocar obturator further comprises a protective tube having a distal end and a proximal end slideably mounted around the trocar obturator, moveable between an extended position and a retracted position, said protective tube being disposed concentrically around said obturator; and biasing means acting on the proximal end of the protective tube to move the tube to the extended position.

36. The method of claim 33 wherein the trocar cannula comprises valve means for sealing off the passage.

37. The method of claim 33 wherein the trocar cannula further comprises sealing means mounted about the entrance to the trocar cannula for sealingly engaging a member inserted therethrough.

38. The method of claim 33, wherein the cannula comprises a transparent material selected from the group consisting of polycarbonates, acrylates, urethanes, polyvinylchlorides, copolymers thereof, clear composite resins, and co-extruded resins.

39. The method of claim 38 wherein the material comprises polycarbonate.

40. The method of claim 33 wherein the cannula walls comprise sufficient thickness to effectively provide mechanical strength while remaining transparent.

41. The method of claim 33 additionally comprising a sufficient amount of a pigment or dye effective to tint the cannula while allowing the interior of the cannula to remain visible through the cannula.

42. In a method of using a trocar cannula in an endosurgical procedure, the trocar cannula comprising an elongate trocar cannula tube and a trocar cannula handle for mounting the tube, the method comprising inserting the trocar cannula into a mammalian body cavity, and using the cannula as a passageway to the body cavity, the improvement comprising using a transparent trocar cannula wherein the interior of the trocar cannula is visible through the trocar cannula and observing the interior of the trocar cannula during at least part of the procedure.

43. The method of claim 42 wherein the trocar cannula comprises valve means for sealing off the passage.

44. The method of claim 42 wherein the trocar cannula further comprises sealing means mounted about the entrance to the trocar cannula for sealingly engaging a member inserted therethrough.

45. The method of claim 42, wherein the cannula comprises a transparent material selected from the group consisting of polycarbonates, acrylates, urethanes, polyvinylchlorides, copolymers thereof, clear composite resins, and co-extruded resins.

46. The method of claim 45 wherein the material comprises polycarbonate.

47. The method of claim 42 wherein the cannula walls comprise sufficient thickness to effectively provide mechanical strength while remaining transparent.

48. The method of claim 42 additionally comprising a sufficient amount of a pigment or dye effective to tint the cannula while allowing the interior of the cannula to remain visible through the cannula.

* * * * *